United States Patent
Chung

[11] Patent Number: 6,038,703
[45] Date of Patent: Mar. 21, 2000

[54] MEN'S BODY TEMPERATURE CONTROLLING PANTS

[76] Inventor: Seun Yung Chung, Kocheung Jukong Apt. 1313-203, Haan 3-Dong, Kwangmyung City, Kyungki-do, 423-060, Rep. of Korea

[21] Appl. No.: 09/091,245
[22] PCT Filed: Dec. 11, 1996
[86] PCT No.: PCT/KR96/00238
  § 371 Date: Jun. 12, 1998
  § 102(e) Date: Jun. 12, 1998
[87] PCT Pub. No.: WO97/21363
  PCT Pub. Date: Jun. 19, 1997

[30] Foreign Application Priority Data

Dec. 12, 1995 [KR] Rep. of Korea .................. 95-41021 U

[51] Int. Cl.⁷ ..................................................... A41B 9/02
[52] U.S. Cl. ..................................................... 2/403; 2/400
[58] Field of Search ............................... 2/400, 401, 402, 2/403, 404, 405; 602/67–71

[56] References Cited

U.S. PATENT DOCUMENTS

| | | | |
|---|---|---|---|
| 4,345,337 | 8/1982 | Chung | 2/405 |
| 4,377,008 | 3/1983 | Jung | 2/403 |
| 4,660,551 | 4/1987 | Nishimura | 2/405 X |
| 4,702,239 | 10/1987 | Ichikawa | 2/403 X |
| 5,283,912 | 2/1994 | Chung | 2/403 |
| 5,555,568 | 9/1996 | Yon | 2/403 |
| 5,618,279 | 4/1997 | Pudlo | 2/403 X |
| 5,647,065 | 7/1997 | Richerson | 2/403 |

FOREIGN PATENT DOCUMENTS

WO 9218021  10/1992  WIPO .................................. 2/403

*Primary Examiner*—Gloria M. Hale
*Attorney, Agent, or Firm*—Wenderoth, Lind & Ponack, L.L.P.

[57] ABSTRACT

Men's pants (shorts or briefs) have a Y type separation band (2) or a U type separation band (22) inside thereof together with separation pads (7, 77) to separate the testicles from the body, the penis from the testicles, and the penis from both hips. Complete separation around the male genitals is achieved without effort by wearing these pants. A penis band (3) formed with an elastic band (4, 44) and clips (5, 55) is sewn to a center part of a waist band (6) in an I shape. A penis hole (14) can be adjusted by moving the two clips (5, 55) up and down according to the individual location and size of the penis (101). A lower part (88) below the clip (5) helps to increase separation between the testicles and the penis.

12 Claims, 2 Drawing Sheets

MEN'S BODY TEMPERATURE CONTROLLING PANTS

BACKGROUND OF THE INVENTION

1. Technical Field

The present invention relates to the promotion of the production of male testosterone by maintaining proper body temperature and testicular temperature, and to the prevention of various skin diseases by airy separation of the body, testicles, penis and hips.

2. Background Art

The present inventor has two previous inventions, including U.S. Pat. No. 5,283,912. The previous inventions had a small hole to separate the testicles from the body, a fixed penis ring to separate the penis from the testicles, and a double waist belt for urination by lowering a front belt attached to a rubbing cloth. Thus the previous invention contributed somewhat to the user's health and hygiene with airiness around the genitals.

Those inventions had some difficulty in separating the testicles from the body with the small hole, which gave an aversion to users. Further, the double belt caused an oppressive feeling to the stomach. The airiness was not so great due to the double structure of the outer cloth and rubbing, except for the hole part. The production cost was also high on account of the double waist belt.

Also, the penis ring of previous inventions was inconvenient to use and insufficient in safety due to its fixed location, regardless of a different size and location of an individual penis. The round ring was deficient in separation and caused aversion.

Moreover, a big problem was that the old and weak had a difficult time using the device due to its complicated structure, and the testicles and penis were apt to slip off due to a lack of caution while using the device.

SUMMARY OF THE INVENTION

The present invention improves the function and addresses the defects of the prior structures. Such improvements involve complete separation of the testicles from the body, and the penis from the testicles and the joints of both hips. The present invention promotes a user's health by maintaining an ideal body temperature at any time and any place and by eliminating sweat around the genitals.

One characteristic of this invention is that a Y or U type separation band is attached to the inside of conventional men's pants, and when in use the testicles are separated automatically without any specific effort. The edge of the Y type separation band is made with an elastic rubber band, and it is flexible with respect to the location of an individual's testicles. Both sides of this band are opened to increase airiness, and two pads are attached to both sides to separate the testicles, body, and hips in case the Y type band sinks to the joint part. The lower part of the Y type separation band functions not only for separation of the hips but for massaging the prostate gland when walking.

A penis band of this invention is made with a double elastic rubber band to be sewn to an upper waist band. Two attached clips are designed to adjust the location and size of the penis hole. Thus, the shape of the penis band looks like the letter I, which does not give any aversion to the user. A lower part below the penis hole increases the width of separation between the penis and testicles.

An advantage of this invention is easy urination by lowering the waist band in a state of separation between the penis and testicles.

DETAILED DESCRIPTION OF THE PREFERRED EMBODIMENTS

Figure 1:
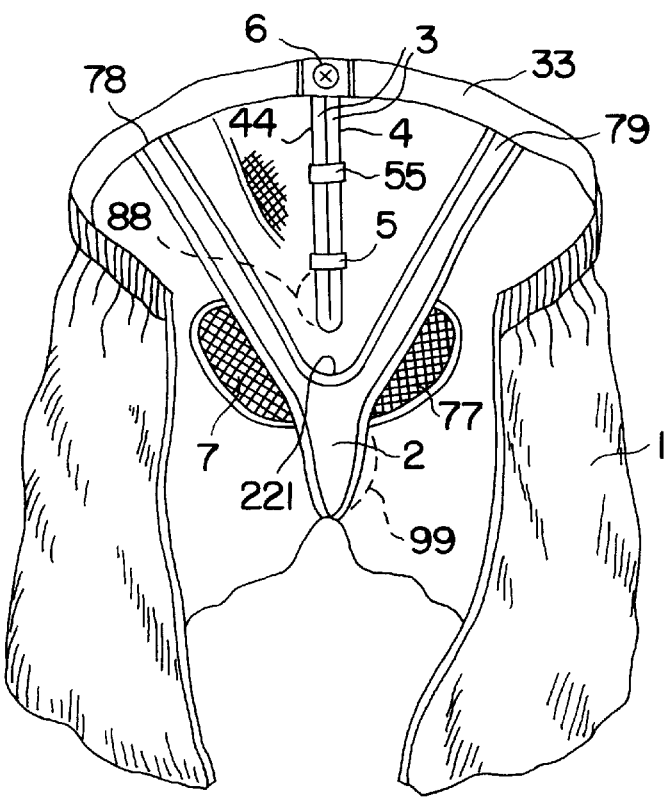
FIG. 1 is a front inside drawing of the present invention shown from a rear side cut of a pair of shorts.
Figure 2:
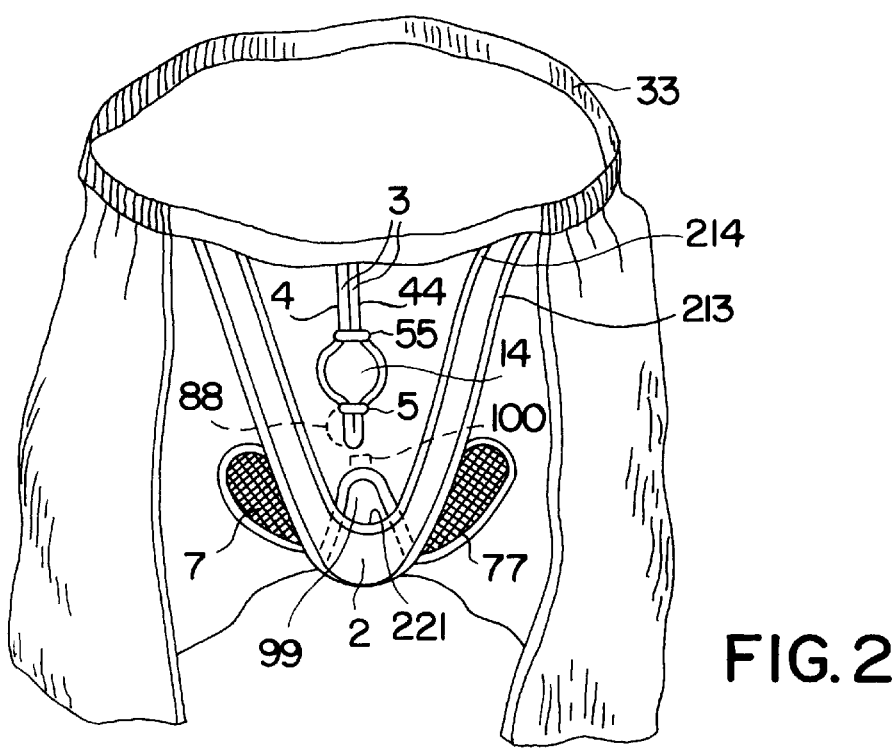
FIGS. 2 and 3 are drawings of an inside separation band shown from a front side cut.
Figure 3:
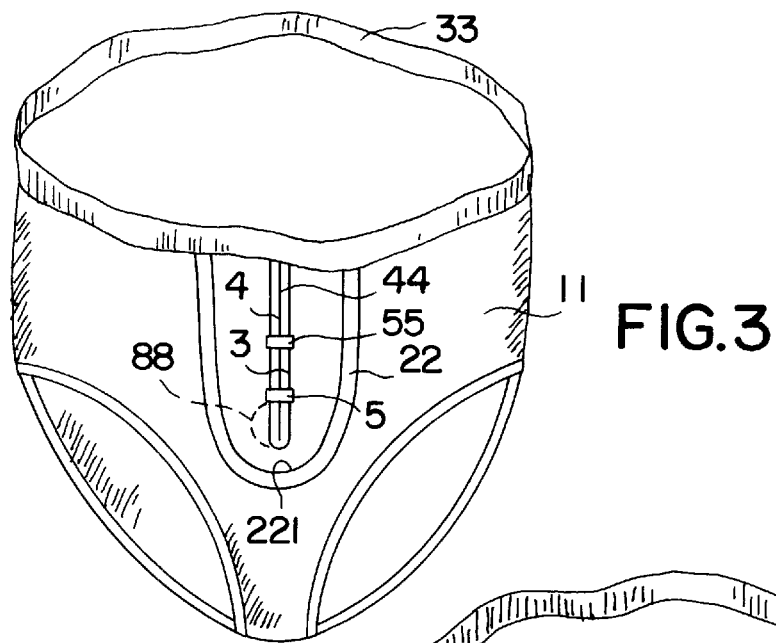
Figure 4:
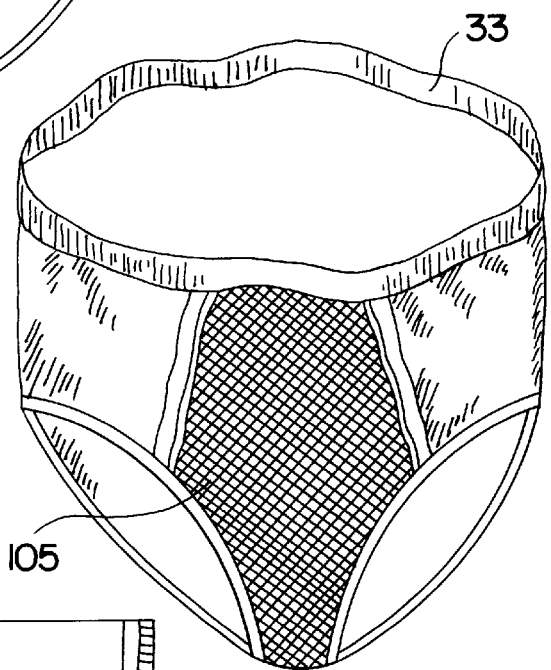
FIG. 4 is an elevation view of a pair of briefs in accord with the present invention.

In FIG. 1, a Y type separation band (2) with an open arched part (221) is to be attached to a pants (shorts) main (1). In FIG. 3, a U type separation band (22) with an open arched part (221) is to be attached to a pants (briefs) main body (11).

The Y type separation band (2) has separation pads (7, 77) attached with it to promote the function of separation. The edge of the separation band (2) is a treated elastic rubber band (213, 214). An upper part (78, 79) of the separation band (2) is to be sewn to a front waist band (33) of the pants. A lower part (99) of the separation band (2) is to be sewn to a hp location (100) inside the rear part of the pants.

The penis band (3) is made with an elastic rubber band (4, 44) in a double I shape. Two clips (5, 55) are applied to the penis band (3), which is sewn to a center part (6) of the waist band.

Figure 5:
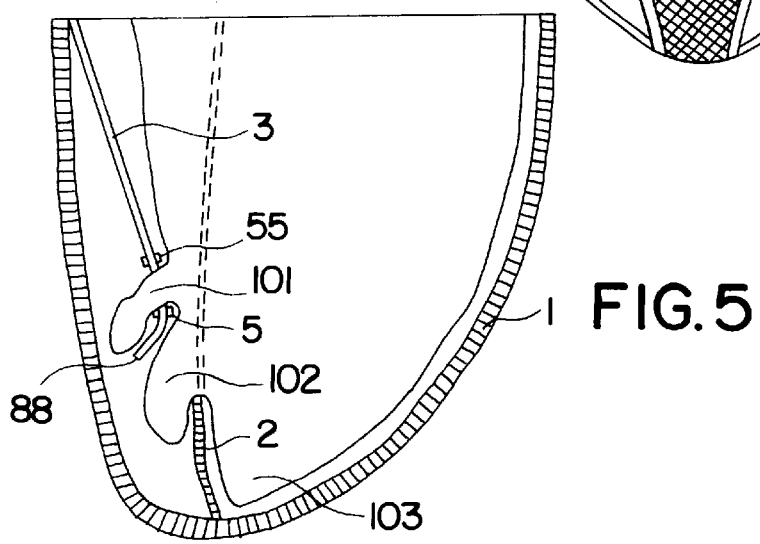
FIG. 5 is a vertical cross sectional view of the invention in use.

Reference number 103 refers to the body. As per FIG. 5, a penis hole is formed with the two clips (5, 55) on the penis band (3). A lower part (88) below the clip (5) widens the width of separation between the penis (101) and the testicles (102).

For the user's convenience, the penis band (3) can be attached to the center part of waist band (6) with a snap button.

In accordance with the above description, the present invention provides men's pants which promote the user's health by maintaining the temperature of the testicles below 33 degrees celsius for a greater production of testosterone, which controls men's energy and vigor, and prevents skin diseases around the genitals byeliminating sweat and increasing airiness.

What is claimed is:

1. Male pants, comprising:
   a pants main body having a front side; and
   a Y shaped separation band on an interior side of said front side of said pants main body positioned to be able to separate the testicles from the body of the wearer when said pants main body is worn by the wearer.

2. The male pants of claim 1, and further comprising separation pads provided with said Y shaped separation band.

3. The male pants of claim 1, and further comprising a penis band on said interior side of said front side of said pants main body, said penis band comprising adjacent band portions having two clips thereon.

4. The male pants of claim 3, wherein said penis band comprises an elastic rubber band attached to a center part of a waist band of said pants main body.

5. The male pants of claim 1, wherein said Y shaped separation band has two legs of its Y shape attached at an upper part of said interior side of said front side of said pants main body and a base of its Y shape attached at a lower part of said pants main body.

6. The male pants of claim 2, wherein said separation pads extend laterally from said Y shaped separation band adjacent to a position at which legs of its Y shape join a base thereof.

7. The male pants of claim 3, wherein said two clips are adjustable in position on said penis band so as to be capable of defining a variably positioned penis hole there between.

8. Male pants, comprising:

a pants main body having a front side; and a U shaped separation band on an interior side of said front side of said pants main body positioned to be able to separate the testicles from the body of the wearer when said pants main body is worn by the wearer.

9. The male pants of claim 8, and further comprising a penis band on said interior side of said front side of said pants main body, said penis band comprising adjacent band portions having two clips thereon.

10. The male pants of claim 9, wherein said penis band comprises an elastic rubber band attached to a center part of a waist band of said pants main body.

11. The male pants of claim 8, wherein said U shaped separation band has two legs of its U shape attached at an upper part of said interior side of said front side of said pants main body.

12. The male pants of claim 9, wherein said two clips are adjustable in position on said penis band so as to be capable of defining a variably positioned penis hole there between.

* * * * *